United States Patent [19]

Knight et al.

[11] 4,431,591
[45] Feb. 14, 1984

[54] 24-NOR-1,4-CHOLADIENE-3,22-DIONE

[76] Inventors: John C. Knight, 4233 N. 8th St., Kalamazoo, Mich. 49007; Merle G. Wovcha, 145 S. Prairie Ave., Kalamazoo, Mich. 49009

[21] Appl. No.: 424,708

[22] Filed: Sep. 27, 1982

Related U.S. Application Data

[62] Division of Ser. No. 291,725, Aug. 10, 1981.

[51] Int. Cl.$^3$ ............................................. C07J 9/00
[52] U.S. Cl. .................................................. 260/397.3
[58] Field of Search ...................................... 260/397.3

[56] References Cited

U.S. PATENT DOCUMENTS 4,201,716  5/1980  Krbechek .................... 260/397.4

FOREIGN PATENT DOCUMENTS 646287  8/1962  Canada ......................... 260/397.4

*Primary Examiner*—Elbert L. Roberts
*Attorney, Agent, or Firm*—Roman Saliwanchik

[57] ABSTRACT

The subject invention concerns a novel fermentation process for making the useful steroid intermediate 24-nor-1,4-choladiene-3,22-dione (I). Compound (I) can be converted to valuable corticoids by known methods.

1 Claim, No Drawings

24-NOR-1,4-CHOLADIENE-3,22-DIONE

This is a division of application Ser. No. 291,725 filed Aug. 10, 1981.

DESCRIPTION

BACKGROUND OF THE INVENTION

U.S. Pat. 4,035,236 discloses and claims the use of *Mycobacterium fortuitum* NRRL B-8119 to make 9-hydroxy-4-androstene-3,17-dione [9-hydroxyandrostenedione]. *M. fortuitum* NRRL B-8119 is a mutant of *M. fortuitum* ATCC 6842. British Pat. No. 1,590,652 discloses the use of *M. fortuitum* NRRL B-8153 to make androsta-1,4-diene-3,17-dione and androst-4-ene-3,17-dione.

BRIEF SUMMARY OF THE INVENTION

Disclosed and claimed is a fermentation process for preparing the useful intermediate 24-nor-1,4-choladiene-3,22-dione (I). This process is conducted by use of a novel mutant of *M. fortuitum* NRRL B-8153. The subject invention process also encompasses the use of novel double mutants obtained from the genera of microorganisms disclosed in U.S. Pat. No. 4,035,236, i.e., Arthrobacter, Bacillus, Brevibacterium, Corynebacterium, Microbacterium, Mycobacterium, Nocardia, Protaminobacter, Serratia, and Streptomyces. The microorganisms of these genera are all well known sterol degraders. The wild type strains of these genera degrade sterols non-selectively to small molecular weight compounds, e.g. $CO_2 + H_2O$. Mutants can be made from these wild types by following the procedures disclosed in U.S. 4,035,236, Example 1.

Mutants of the genera, disclosed above, which can be made by using the procedures of Example 1 of U.S. 4,035,236, can then be subjected to the mutation procedures, disclosed herein, to prepare further mutants. These latter mutants, as exemplified here by *M. fortuitum* NRRL B-12505, can be used in the fermentation process, disclosed herein, to prepare compound (I).

DETAILED DESCRIPTION OF THE INVENTION

The Microorganisms

Mutants which are characterized by their ability to selectively degrade steroids having C-17 side chains and accumulate 24-nor-1,4-choladiene-3,22-dione (I) as a major product in the fermentation beer can be obtained by mutating microorganisms of the following genera: Arthrobacter, Bacillus, Brevibacterium, Corynebacterium, Microbacterium, Mycobacterium, Nocardia, Protaminobacter, Serratia, and Streptomyces.

Following is an example of the preparation of the novel mutant used in the subject fermentation process. The mutant prepared in this example is *M. fortuitum* NRRL B-12505. Similar mutants from other Mycobacterium species and other microbe genera, as recited herein, can be prepared by following the procedures of the following example.

Preparation of a mutant which accumulates 24-nor-1,4-choladiene-3,22-dione as a major product of the degradation of sterols

*Mycobacterium fortuitum* NRRL B-8153 is grown at 31° in a medium consisting of (per liter) nutrient broth, 8 g; yeast extract, 1 g; glycerol, 5 g; Tween 80, 0.1% (w/v); and distilled $H_2O$. This medium is sterilized by autoclaving at 15 lb/in$^2$ for 20 min. The cells are grown to a density of about $5 \times 10^8$ per ml, and then collected on a sterile 0.2 micron filter. The cells are washed with an equal volume of sterile 0.1 M sodium citrate, pH 5.6 containing 0.1% Tween 80, and then resuspended in $\frac{1}{2}$ volume of the same buffer. N-methyl-N'-nitro-N-nitrosoguanidine is added to a concentration of 100 μg/ml and the cell suspension is incubated at 31° C. for 1 hr. The cells are then washed with 2 volumes of sterile 0.1 M potassium phosphate buffer, pH 7 containing 0.1% Tween 80, and then resuspended in 1 volume of the same buffer. A medium is prepared containing (per liter) nutrient broth, 8 g; NaCl, 5 g; glycerol, 5 g; and distilled $H_2O$. Agar is added to 15 g/l and the medium is autoclaved at 15 lb/in$^2$ for 20 min and then poured into sterile Petri dishes. The mutagenized cells are then plated on this medium and colonies which grow on these plates are subsequently screened in small scale fermentations for their ability to convert sterols to compound (I). Detection of the desired compound is by thin layer chromatography of methylene chloride extracts of the test fermentations, using silica gel and the solvent system methylene chloride-acetone-acetic acid (212-38-1). In this manner, mutant NRRL B-12505 is isolated which accumulates 24-nor-1,4-choladiene-3,22-dione as a major product of the bioconversion of sterols.

The key to isolating a mutant like the one described herein is to start with a mutant, such as NRRL B-8153, which is already blocked in steroid ring degradation so that it produces androsta-1,4-diene-3,17-dione and introduce into this microorganism a second mutation affecting sterol side chain degradation.

Description of the Microorganism

The mutant bringing about the biotransformation described herein differs from its parent culture, e.g., *Mycobacterium fortuitum* NRRL B-8153, only in its action on steroid molecules. In all other respects, such as morphology and drug sensitivities, they are similar if not identical. Both *M fortuitum* cultures are acid-fast non-motile, non-sporulating bacilli belonging to the family Mycobacteriaceae of the order Actinomycetales. According to Runyon's classification, Runyon, E. H., 1959 Med. Clin. North America 43:273, it is a non-chromogenic group IV mycobacterium, i.e., it grows rapidly at low temperature to produce nonpigmented colonies on relatively simple media.

*M. fortuitum* NRRL B-8153 and NRRL B-12505 have been deposited in the permanent collection at the Northern Regional Research Laboratory, U.S. Department of Agriculture, Peoria, Illinois, U.S.A. *M. fortuitum* NRRL B-8153 was deposited prior to November, 1977, and *M. fortuitum* NRRL B-12505 was deposited on July 28, 1981. Subcultures of these microorganisms are available from the NRRL depository by request made thereto. It should be understood that the availability of the culture does not constitute a license to practice the subject invention in derogation of patent rights granted with the subject instrument by governmental action.

Compound (I) is useful as an intermediate in the synthesis of valuable corticoids. For example, preparation of an enol ether or enamine of the 22-keto group, followed by oxidation of the 20(22)-double bond gives 1-dehydroprogesterone, which can be converted to corticosteroids by well-known processes. See Chart 2.

Following are examples which illustrate the fermentation process of the subject invention. These examples are merely illustrative, and, thus, should not be construed as limiting. All percentages are by weight and all solvent mixture proportions are by volume unless otherwise noted.

EXAMPLE 1—FERMENTATION OF CRUDE SITOSTEROL

The biotransformation medium contains (per liter) Ucon, 8.0 g; Cerelose, 5.0 g; $NH_4Cl$, 3.0 g; $CaCO_3$, 3.0 g; $Na_3$ [citrate].$2H_2O$, 3.0 g; Tween 80, 2.0 g; soyflour, 1.0 g; $KH_2PO_4$, 0.5 g; urea, 0.5 g and crude sitosterol, 30.0 g in tap water with the pH adjusted to 7.0. Flasks containing 100 ml portions of this medium are innoculated with 10 ml of seed cultures of *M. fortuitum* NRRL B-12505, grown at 31° in a medium containing (per liter) nutrient broth, 8.0 g; glycerol, 5.0 g; yeast extract, 1.0 g and Tween 80, 1.0 g in distilled water with the pH adjusted to 7.0. The cultures are then incubated at 31° for 168 hr on a rotary shaker. Following incubation, the mixture is extracted and the product isolated as detailed below in Example 3.

EXAMPLE 2

Just as in Example 1, but with various steroidal substrates provided singly or in combination and in pure or crude form. Such substrates include sitosterol, cholesterol, stigmasterol and campesterol.

EXAMPLE 3

Isolation of (I) from *M. fortuitum* NRRL B-12505 Fermentation

Fermentation beer (600 ml) from a sitosterol bioconversion using *M. fortuitum* NRRL B-12505 is extracted with an equal volume of methylene chloride ($MeCl_2$), and the crude extract evaporated to yield a sticky brown solid. This is recrystallized from acetone/water to give two successive crops of unconverted sitosterol, totalling 15.4 grams. The mother liquor is concentrated to an aqueous emulsion in vacuo, and extracted with methylene chloride. The residue obtained on removal of the solvent is redissolved in ethyl acetate and left to crystallize overnight. The crystals that separate (1.44 g) consist largely of the less polar UV-active bioconversion product. Purification is completed by chromatography on silica in ethyl acetate/cyclohexane 40:60, which gives the 24-nor-1,4-choladiene-3,22-dione as a colorless solid, crystallizing from ethyl acetate as needles (550 mg), mp 221°-222.2°, $[a]_D$—23° (C, 1.0195; $CHCl_3$). The ir spectrum shows saturated and unsaturated ketone peaks at 1712 and 1656 $cm^{-1}$, and the $^1H$.nmr spectrum gives the characteristic peaks of the 1,4-diene-3-one system. In addition to the signals for the 18- and 19-methyl groups (0.78 and 1.24 δ) there is a strong singlet at 2.12 typical of an acetyl methyl, and a doublet at 1.14 due to the secondary methyl at C-21. The mass spectrum indicates a molecular weight of 340 ($C_{23}H_{32}O_2$). A fragment ion at m/e 297 (M-43) shows loss of $CH_3CO$—, and one at m/e 268 (M-72) indicates loss of a four carbon side-chain from the steroid nucleus. These data point to structure I as the main UV-active product of this fermentation.

EXAMPLE 4

By substituting a sterol-degrading microorganism from the genera Arthrobacter, Bacillus, Brevibacterium, Corynebacterium, Nocardia, Protaminobacter, Serratia, and Streptomyces, for *Mycobacterium fortuitum* NRRL-8153 in the process disclosed for preparing *M. fortuitum* NRRL B-12505, there are obtained mutant microorganism which are characterized by their ability to selectively degrade steroids with a C-17 side chain and accumulate compound (I) as a major product.

EXAMPLE 5

By substituting the mutants obtained in Example 4 for *M. fortuitum* NRRL B-12505 in Example 1, there is obtained compound (I).

CHART 1

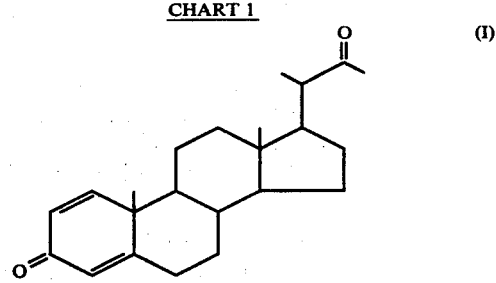

CHART 2

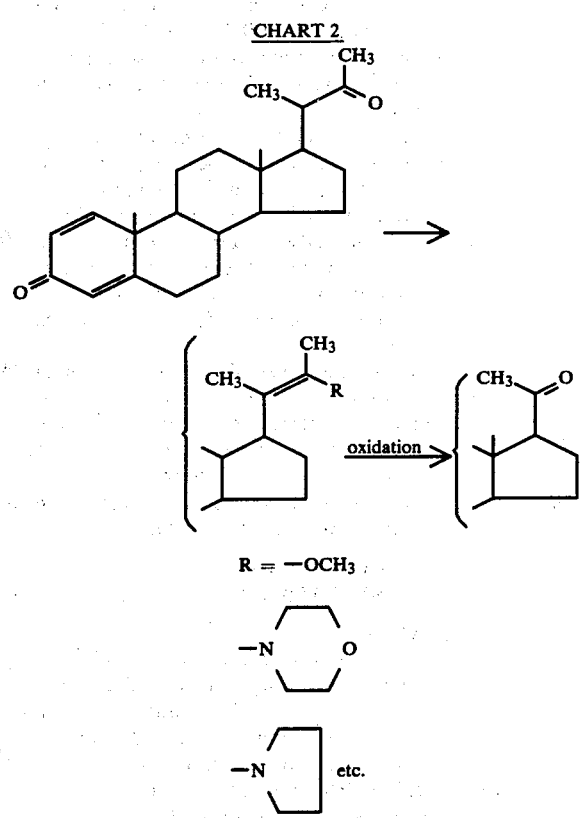

We claim:
1. A novel compound of the formula

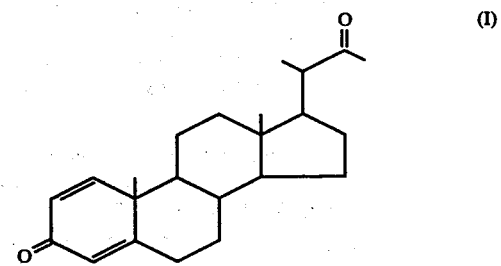

* * * * *

UNITED STATES PATENT OFFICE
CERTIFICATE OF CORRECTION

Patent No. 4,431,591    Dated February 14, 1984

Inventor(s) John C. Knight and Merle G. Wovcha

It is certified that error appears in the above-identified patent and that said Letters Patent are hereby corrected as shown below:

On front page of the patent, after Inventors insert:

-- [73] Assignee: The Upjohn Company, Kalamazoo, Mich.--

Signed and Sealed this

First Day of May 1984

[SEAL]

Attest:

GERALD J. MOSSINGHOFF

Attesting Officer

Commissioner of Patents and Trademarks